United States Patent [19]

Singh et al.

[11] Patent Number: 5,652,234
[45] Date of Patent: Jul. 29, 1997

[54] 3-(7-OXO-1-AZA-4-OXABICYCLO[3.2.0]HEPT-3-YL)ALANINE DERIVATIVE AS ANTITUMOR AGENT

[75] Inventors: Rajeshwar Singh, Alberta, Canada; Tomohiro Yamashita, Hidaka, Japan; Charles Fiakpui, Alberta, Canada; George Thomas, Alberta, Canada; Chan Ha, Alberta, Canada; Hiroshi Matsumoto; Toshio Otani, both of Tokushima, Japan; Shinji Oie, Tokyo, Japan; Ronald Micetich, Alberta, Canada

[73] Assignees: Taiho Pharmaceutical Co., Limited, Tokyo, Japan; SynPhar Laboratories, Inc., Edmonton, Canada

[21] Appl. No.: 513,803

[22] PCT Filed: Jan. 6, 1995

[86] PCT No.: PCT/GB95/00023

§ 371 Date: Oct. 6, 1995

§ 102(e) Date: Oct. 6, 1995

[87] PCT Pub. No.: WO95/18611

PCT Pub. Date: Jul. 13, 1995

[30]  Foreign Application Priority Data

Jan. 7, 1994 [GB]  United Kingdom ............... 9400239

[51] Int. Cl.$^6$ .................................................. A61K 31/395
[52] U.S. Cl. .................................................. 514/210
[58] Field of Search .................................................. 514/210

[56]  References Cited

PUBLICATIONS

Database WPI Week 8644, Derwent Publications Ltd., Londgon, GB; AN 86–289067 (1986).
*Chinese J. Antibiot.*, vol. 16, No. 1, 1991, pp. 1–13, "A study of new clavam antibiotics G0069." pp. 8–13 only.

*Primary Examiner*—Jerome D. Goldberg
*Attorney, Agent, or Firm*—Nikaido, Marmelstein, Murray & Oram LLP

[57]  ABSTRACT

The present invention relates to the use of 3-(7-oxo-1-aza-4-oxabicyclo[3.2.0]hept-3-yl)alanine derivatives of formula (I) or a pharmaceutically acceptable salt thereof, as antitumor agents.

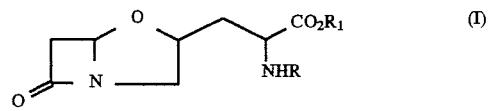

Wherein R is:
hydrogen or $COOR_2$ wherein $R_2$ is $C_1$–$C_3$ alkyl group which may be substituted with aryl group.

Wherein $R_1$ is:
hydrogen or $C_1$–$C_3$ alkyl group which may be substituted with one or two aryl groups.

11 Claims, No Drawings

3-(7-OXO-1-AZA-4-OXABICYCLO[3.2.0]HEPT-3-YL)ALANINE DERIVATIVE AS ANTITUMOR AGENT

This invention relates to the use of 3-(7-oxo-1-aza-4-oxabicyclo[3.2.0]hept-3-yl) alanine derivatives as antitumor agents.

BACKGROUND OF INVENTION

Since the isolation and structural elucidation of natural β-lactamase inhibitor clavulanic acid, a number of naturally occurring metabolites, G0069A (JP 61-212587), Tü 1718 (DE 3727651 A1), Clavamycin (J. of Antibiotic 39, 510 (1986)), Ibid 39, 516 (1986)), Ro 22-5417 (J. of Antibiotic 36, 217 (1983)) have been isolated from the culture of genius streptomyces. None of the above metabolites exhibited β-lactamase inhibitory properties. However, in most cases, attention was paid to their antibacterial and antifungal activity.

We paid attention to develop G0069A (JP 61-212587) as antitumor agent. However, there were a lot of difficulties in obtaining this compound in large scale. For example, only 20 mg of G0069A was isolated from 10L of fermentation broth even after being under well controlled fermentation technique and suitable experimental conditions.

G0069A is a chemicalyl unstable isolation process and required very complex and special techniques. This should be done in the dark at low temperatures. In addition to the above complexity in isolation of G0069A from fermentation broth, the synthetic approach also seemed to be an extremely difficult multi-step process because they have 5-asymmetric carbon centres and dipeptide side chain. Therefore, it is necessary to get compounds which are relatively easy to synthesize, have shorter chains than G0069A, chemically stable and have stronger antitumor activity.

SUMMARY OF THE INVENTION

The present invention relates to an antitumor composition comprising of an effective amount of the 3-(7-oxo-1-aza-4-oxabicyclo[3.2.0]hept-3-yl)alanine derivative represented by the formula (I) or a pharmaceutically acceptable salt thereof

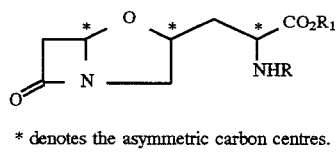

\* denotes the asymmetric carbon centres.

and a pharmaceutically acceptable carrier, wherein R is:

hydrogen or $COOR_2$, wherein $R_2$ is $C_1$–$C_3$ alkyl group which may be substituted with 1–3 aryl groups;

wherein $R_1$ is:

hydrogen or $C_1$–$C_3$ alkyl group which may be substituted with 1–3 aryl groups.

Example of $C_1$–$C_3$ alkyl group as substituent in $R_1$ and $R_2$ are methyl, ethyl, propyl or isopropyl.

More specifically, R in general formula (I) is selected from hydrogen, methoxycarbonyl, ethoxycarbonyl or benzyloxycarbonyl, and $R_1$ is selected from hydrogen, methyl, benzyl, diphenylmethyl or triphenylmethyl.

Examples of pharmaceutically acceptable salts are sodium, potassium, calcium, magnesium, hydrogen chloride, tartaric, fumaric, maleic, acetic, trifluoroacetic, citric, methanesufonic, trifluoromethanesulfonic, p-toluenesufonic and so on.

The present invention provides a method of treating tumors in mammalian animals which comprises of administering to mammalian animals having tumors with an effective amount of the derivative of formula (I).

Furthermore, the present invention provides use of the derivative of formula (I) for the preparation of a pharmacological composition for treatment of tumors.

The bicyclic nucleus carries two asymmetric carbon atoms at position 3 and 5 and can exist as 4-diastereoisomers. In general, the preferred isomer is (3R, 5S) and (3S,5R) or mixture of them for superior toxicity against different malignant cells such as P388, KB, NUGC4, WI38, L-1210, sarcoma 180 and colon 26. Such diastereoisomers and their mixtures are also included within the use of oxapenam derivatives as antitumor agents.

The chain alanine at $C_3$ of bicyclic nucleus carries one asymmetric carbon atom having D and L isomers. Both of the isomers (D and L) are included within the use of oxapenam derivatives as antitumor agents.

Antitumor activity of the compounds described above is expected against some solid cancers such as gastrointestinal tract, lung, breast, liver, uterus and leukemia and so on.

DESCRIPTION OF PREFERRED EMBODIMENTS

The present invention relates to the use of oxapenam derivatives having excellent antitumor activity. The compounds of this invention are characterized by the general formula (I)

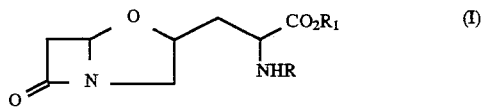

The synthesis of the compound of general formula (I) was done by following the synthetic scheme as shown below using DL-allyl-glycine as a starting material.

SCHEME

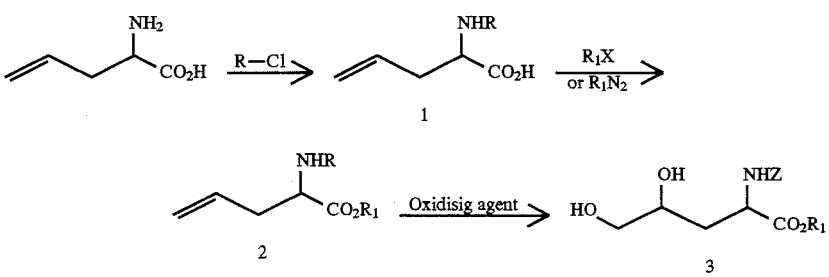

-continued
SCHEME

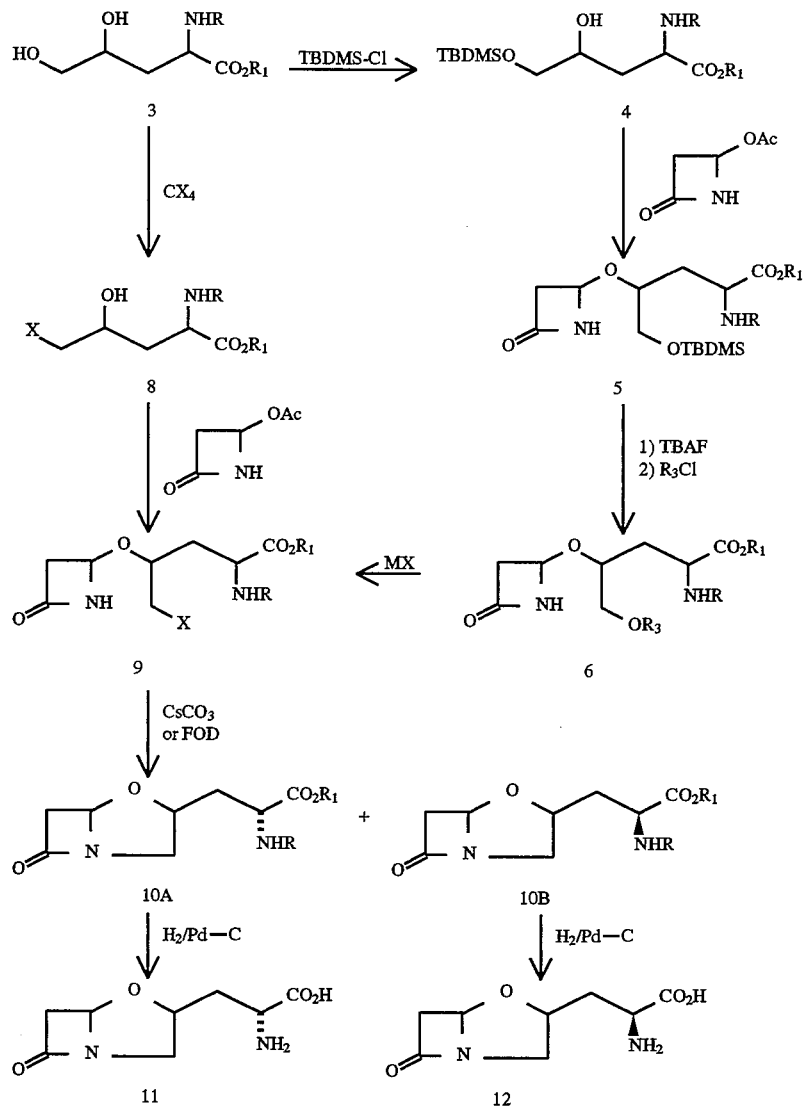

TBDMS: t-Butyldimethylsilyl; TBAF: Tetrebutylammonium fluoride.

The R and $R_1$ are the same as defined above.

The $R_3$ is substituted sulfonyl group such as methanesulfonyl, trifluoromethanesulfonyl, bezenesulfonyl, 4-chlorobenzenesulfonyl, p-toluenesulfonyl, and so on.

X is halogen atom such as fluorine, bromine, chlorine or iodine.

M is metal such as sodium, potassium, lithium, and so on.

In the above descriptions, the reactants are reacted together with solvent at elevated or low temperatures for sufficient time to allow the reaction to proceed to completion. The reaction conditions depend upon the nature and reactivity of the reactants. Wherever base is used in the reaction, they are selected from triethylamine, pyridine, 4-diaminopyridine, diisopropylethylamine, 2,6-colidine, imidazole, piperidine, piperadine, pyrrolidine, morpholine, 1,8-diazabicyclo[5.4.0.]undec-7-ene, 1,5-diazabicyclo-[4.3.0]non-5-ene, sodium carbonate, potassium carbonate, lithium carbonate, cesium carbonate sodium hydrogen carbonate, potassium hydrogen carbonate, lithium hydrogen carbonate, cesium hydrogen carbonate and so on.

The solvents of choice for the reactions are non reactive solvents such as acetonitrile, tetrahydrofuran, ethanol, methanol, benzene, chloroform, ethyl acetate, acetone, methylene chloride, water, dimethylformamide, dimethylsulfoxide, hexamethylphosphoric triamide, or the like. Solvent mixtures may also be utilized.

Reaction temperatures would generally range from between −20° C. to 140° C. The preferred molar ratio of the reactants are 1:1 to 5.0. The reaction time range is from 0.5 to 72 h, depending on the reactants.

The oxidizing agents are used for dihydroxylation of double bonds and are selected from either osmium tetroxide, potassium osmate, potassium permanganate, t-butyl hydroperoxide, hydrogen peroxide, AD mix-α, or AD mix-β. The AD mix-α and β may be used to prepare chiral diol 3 (J. Org. Chem. 57, 2768 (1992); Tetrahedron Lett. 34, 2267 (1993)).

The deprotection of N and O protective group is carried out either by hydrogenation or by hydrolysis with mineral acids like hydrochloric acid in solvent like methanol, ethanol, propanol, ethyl acetate. The hydrogenation reaction is usually carried out in the presence of a metal catalyst such as Pd, Pt, Rh under normal pressure to high pressure of hydrogen.

The structure of the compounds were established by the mode of synthesis and by extensive high field nuclear magnetic resonance spectral technique. The NMR spectra of compound 11 was the same as described by De Bernardo et al. (J. Org. Chem. 50, 3457 (1985)).

The compound of the invention, when used as an agent for treating malignant tumors of mammals including humans, may take pharmaceutical dosage forms including parenteral preparations such as injections, suppositories, aerosols and the like and oral preparations such as tablets, coated tablets, powders, granules, capsules, liquids and the like. Injections are generally preferred. The above preparations are formulated in a manner known in the art.

For the formulation of solid preparations for oral administration an excipient, and if desired, a binder, disintegrator, lubricant, coloring agent, corrigent, flavor, etc. are added to the compound of the invention, and then tablets, coated tablets, granules, powders, capsules or the like are prepared in a conventional manner.

For the formulation of injections, a pH adjusting agent, buffer, stabilizer, isotonic agent, local anesthetic or the like is added to the active ingredient of the invention, and injections for subcutaneous, intramuscular or intravenous administration can be prepared in a conventional manner.

For the formulation of suppositories, a base, and if desired, a surfactant are added to the active ingredient of the invention, and the suppositories are prepared in a conventional manner.

The excipients useful for the solid preparations for oral administration are those generally used in the art and useful examples are excipients such as lactose, sucrose, sodium chloride, starches, calcium carbonate, kaolin, crystalline cellulose, methyl cellulose, glycerin, sodium alginate, gum arabic and the like, binders such as polyvinyl alcohol, polyvinyl ether, polyvinyl pyrrolidone, ethyl cellulose, gum arabic, schellac, sucrose, water, ethanol, propanol, carboxymethylcellulose, potassium phosphate and the like, lubricants such as magnesium stearate, talc and the like, and further include additives such as usual known coloring agents, disintegrators and the like. Examples of bases useful for the formulation of suppositories are oleaginous bases such as cacao butter, polyethylene glycol, lanolin, fatty acid triglycerides, Witepsol (trademark, Dynamite Nobel Co., Ltd.) and the like. Liquid preparations may be in the form of aqueous or oleaginous suspension, solution, syrup, elixir and the like, which can be prepared by a conventional way using usual additives.

The amount of the compound (I) of the invention to be incorporated into the pharmaceutical composition of the invention varies with the dosage form, solubility and chemical properties of the compound, administration route, administration scheme and the like. Preferably the amount is about 1 to 25 w/w % in the case of oral preparations, and about 0.1 to about 5 w/w % in the case of injections which are parenteral preparations.

The dosage of the compound (I) of the invention is suitably determined depending on the individual cases taking symptom, age and sex of the subject and the like into consideration. Usually, the dosage in the case of oral administration is about 50 to about 1000 mg per day for an adult in 2 to 4 divided doses, and the dosage in the case of injection, for example, by intravenous administration is 2 ml (about 1 to about 50 mg) which is administered once a day for an adult wherein the injection may be diluted with physiological saline or glucose injection liquid if so desired, and slowly administered over at least 5 minutes. The dosage in the case of suppositories is about 1 to about 500 mg which is administered once or twice a day at an interval of 6 to 12 hours wherein the suppositories are administered by insertion into the rectum.

Given below are Preparation Examples. In the Preparation Examples that follow, the compound numbers correspond to the compound numbers used in the Reference Examples to be described later.

| Preparation Example 1: Tablets | |
|---|---|
| Compound 11 | 50 g |
| Lactose | 200 g |
| Corn starch | 80 g |
| Hydrolyzed starch | 20 g |
| Potassium stearate | 10 g |
| | 360 g |

Compound 11, lactose, corn starch and hydrolyzed starch were mixed, and granulated by adding water to prepare an active paste. After drying overnight at 45° C., the granules were sieved. Potassium stearate was added thereto and the tablets weighing 360 mg and having a diameter of 10 mm were produced by means of tabletting machine.

| Preparation Example 2: Capsules | |
|---|---|
| Compound 11 | 25.0 g |
| Lactose | 150.0 g |
| Corn Starch | 40.0 g |
| Talc | 5.0 g |
| Per capsule | 200.0 mg |

Compound 11, lactose and corn starch were mixed and pulverized. After addition of talc, the mixture was placed into hard gelatin capsules.

Preparation Example 3: Injections

To Compound 11 (50 g) and 400 g of glucose was added distilled water for injection with stirring until the total volume became 10 liters. The mixture was filtered for sterilization and placed into ampoules, and nitrogen gas was aerated therein followed by sealing, thereby producing injection preparations each having a volume of 10 ml per ampoule.

Preparation Example 4: suppository form

"Wirepsol W-35" (trademark, product of Dynamite Nobel Co., Ltd., West Germany) was fused at about 60° C. and the solution was maintained at about 45° C. The solution and the compound 6 was mixed in the following proportions and shaped into a suppository form weighing 1 g each with use of suitable suppository-forming device.

| Components | mg/suppository |
|---|---|
| Compound 11 | 400.0 |
| Witepsol W-35 | 600.0 |
| | 1,000.0 |

The compounds of general formula (I), required for the use as antitumor activity, were prepared by the procedure either as described in literature or within the skill of art. The compounds which have been used in this invention as antitumor agents, are reported as reference examples.

REFERENCE EXAMPLE 1

N-Benzyloxycarbonyl-(DL)-allylglycine (1)

$NaHCO_3$ (37.95 g, 450 mmol) was added to a suspension of allylglycine (5.2 g, 45 mmol) in a mixture of $THF-H_2O$ (1:3) (80 ml). The mixture was cooled no −10° C. and benzylchloroformate (11.6 g, 67 mmol) was added dropwise while maintaining the pH aapproximately 8 by the addition of saturated aqueous NaHCO₃ solution. The mixture was stirred overnight and diluted with ether (100 ml). The ether portion was separated and the aqueous portion was cooled in an ice bath. Acidification with conc. HCl was followed by extraction with ethyl acetate (3×150 ml). The ethyl acetate solution was dried (MgSO₄) and the solvent was removed in vacuo to give pure 1 (7.9 g, 70%) as a thick oil.

$^1$H NMR (CDCl₃, 200 MHz) δ: 2.56 (2H, m) ; 4.48 (1H, m) ; 5.12 (2H, s); 5.17–5.34 (3H, m); 5.71 (1H, m); 7.34 (5H, s); 8.20 (1H, br. s).

IR (Neat): 3325, 3185, 3075, 2950, 1719, 1709, 1582, 1521 cm⁻¹.

REFERENCE EXAMPLE 2

N-Benzyloxycarbonyl-(DL)-allylglycine diphenylmethyl ester(2)

A solution of diphenyldiazomethane (1.4 g, 7.2 mmol) in dichloromethane (30 ml) was added dropwise to a solution of N-benzyloxycarbonyl-(DL)-allylglycine (1.8 g, 7.22 mmol) in dichloromethane (50 ml). After the addition, the solvent was concentrated and the product was purified by a silica gel column chromatography using hexane-ethyl acetate (4:1) as the eluant gave 2 (2.2 g, 75%) as oil.

$^1$H NMR (CDCl₃, 200 MHz) δ: 2.57 (2H, m); 4.5 m); 4.96–5.04 (2H, m); 5.09 (2H, s); 5.31 (1H, d, J=8.0 Hz); 5.45–5.65 (1H, m); 6.90 (1H, s); 7.31 (15H, m).

IR (Neat): 3345, 3175, 3035, 1728, 1719 cm⁻¹.

REFERENCE EXAMPLE 3

Diphenylmethyl 2-N-benzyloxycarbonylamino-4,5-dihydroxypentanoate (3)

N-methylmorpholine N-oxide (12.6 ml) and osmium tetraoxide (4% wt soln. in water) (5 ml) was added to a solution of (DL)-N-(benzyloxycarbonyl)-allylglycine diphenylmethyl ester (25.57 g, 61.5 mmol) in water (30 ml) —acetone (240 ml). The mixture was stirred overnight and quenched with saturated sodium bisulfite solution (50 ml). After stirring for 10 minutes, the mixture was extracted with ethyl acetate (3×150 ml), washed with brine, dried (MgSO₄) and the solvent was removed in vacuo. Purification by a silica gel column chromamography using hexane-ethyl acetate (1:4) as The eluant gave 3 (20.74 g, 70%) as oil.

$^1$H NMR (CDCl₃, 200 MHz) δ:(Mixture of stereoisomers) 1.93 (2H, m); 2.35–2.56 (1H, br.s); 3.30–3.96 (4H, m); 4.50–4.82 (1H, m); 5.15 (2H, s); 5.89 (1H, br.s); 6.96 (1H, s); 7.30 (15H, m).

IR (Neat): 3390, 3340, 2935, 1772, 1737, 1712 cm⁻¹.

REFERENCE EXAMPLE 4

Diphenylmethyl 2-N-benzyloxycarbonylamino-5-(t-butyldimethylsilyl)oxy-4-hydroxypentanoate (4)

Imidazole (0.903 g, 13.2 mmol) and tert-butyldimethylsilyl chloride (2.31 g, 15.3 mmol) was added to an ice-cold solution of the diol 3 (4.59 g, 10.2 mmol) in dichloromethane (100 ml). After the addition, the mixture was stirred at room temperature overnight and diluted with dichloromethane (50 ml). The dichloromethane solution was washed with water (2×100 ml), brine (2×100 ml), dried (MgSO₄) and the solvent was removed in vacuo. Purification by silica gel column using hexane-ethyl acetate (3:2) as eluant gave 4 (4.1 g, 75%) as an oil.

$^1$H NMR (CDCl₃, 200 MHz) δ: 0.03 (6H, s) ; 0.87 (9H, s) ; 1.92 (2H, m); 3.08 (1H, br.s); 3.43 (2H, m); 3.55 (1H, m); 4.70 (1H, m); 5.17 (2H, s); 5.90 (1H, br.s); 6.90 (1H, s); 7.33 (15H, m).

IR (Neat): 3395, 3065, 2955, 1782, 1722 cm⁻¹.

REFERENCE EXAMPLE 5

Diphenylmethyl 2-N-benzyloxycarbonylamine-4-(azetidin-2-one-4-yl)oxy-5-(t-butyl-dimethylsilyl) oxypentanoate (5)

Triethylamine (8.19 g, 81 mmol) and palladium (II) acetate (1.82 g, 8.1 mmol) was added to a solution of 4-acetoxyazetidinone (10.52 g, 81 mmol) and the alcohol 4 (21.83 g, 41 mmol) in benzene (500 ml). The mixture was stirred at room temperature under nitrogen atmosphere for 20 hr and filtered through a pad of celite. The celite was washed with ethyl acetate (300 ml) and the combined organic layer was washed with brine (3×150 ml), dried (MgSO₄) and the solvent was removed in vacuo. Purification by silica gel column chromatography using hexane-ethyl acetate (1:1) as eluant gave ≧(16.76 g 55%) as a foam.

$^1$H NMR (CDCl₃, 200 MHz) δ:(3:1 mixture of diastereomers) 0.03 (6H, s), 0.87 (9H, s); 1.75–1.94 (2H, m); 2.79–3.07 (2H, m); 3.46–3.69 (3H, m); 4.53–4.76 (1H, m); 4.96 (1H, m); 5.09 (2H, s); 5.52–5.60 (1H, br); 6.30–6.45 (1H, br.s); 5.88 (1H, br.s; 7.32 (15H, m).

IR (Neat): 3325, 3065, 3044, 2955, 1775, 1737m 1521 cm⁻¹.

REFERENCE EXAMPLE 6

Diphenylmethyl 2-N-benzyloxycarbonylamino-5-hydroxy-4-(azetidin-2-one-4-yl)oxypentanoate (6)

Tetrabutylammonium fluoride (1M solution in THF) (40 ml, 46.2 mmol) and glacial acetic acid (5 ml) was added to an ice-cold solution of silyloxy compound 5 (19.5 g, 30.8 mmol) in THF (200 ml). After the addition, the mixture was stirred at room temperature for 4 h. The solvent was concentrated and the residue was loaded onto a silica gel column. Elution with hexane-ethyl acetate (1:1) removed impurities. The desired alcohol 6 (10.1 g, 63%) was obtained as foam after eluting with ethyl acetate-acetone (4:1).

$^1$H NMR (CDCl₃, 200 MHz) (Mixture of diastereomers) δ: 1.85–1.99 (2H, m); 2.61–2.92 (2H, m); 3.46–3.69 (3H, m); 4.29 (1H, br.s); 4.78 (1H, m); 4.98–5.07 (3H, m); 6.78 (1H, s); 7.36 (15H, s); 7.81 (1H, br.s); 8.38 (1H, br.s).

IR (Neat): 3385, 3060, 2930, 1743, 1736, 1583, 1514 cm⁻¹.

REFERENCE EXAMPLE 7

Diphenylmethyl 2-N-benzyloxycarbonylamino-4-(azetidin-2-one-4-yl)oxy-5-(p-toluenesulfonyloxy) pentanoate (7)

p-Toluenesulfonyl chloride 14.96 g, 26 mmol) was added to a solution of the alcohol 6 (9.0 g, 17.2 mmol) in pyridine (42 ml) cooled to −10° C. The resulting mixture was stirred for 4 h and poured onto a cold 2N HCl (600 ml) solution. The mixture was extracted with ethyl acetate (3×200 ml) and the ethyl acetate portion was washed with water (100 ml), brine, dried (MgSO₄) and the solvent was removed in vacuo. Purification by silica gel column chromatography using hexane-ethyl acetate (1:1) as the eluant gave 7 (9.92 g, 85%) as white foam.

$^1$H NMR (CDCl₃, 200 MHz) (Mixture of diastereomers) δ: 1.75–1.98 (2H, m); 2.40 (3H); 2.50 (1H, m); 2.85 (1H, m); 3.76 (1H, m); 3.99–4.22 (3H, m); 4.96–5.06 (3H, m); 6.78 (1H, s); 7.35 (17H, m); 7.77 (3H, m); 8.39 (1H, br.s).

REFERENCE EXAMPLE 8

Diphenylmethyl 2-N-benzyloxycarbonylamino-5-bromo-4-hydroxypentanoate (8)

A solution of triphenylphosphine (2.0 g, 7.5 mmol) in dichloromethane (10 ml) was added to an ice-cold solution of the diol 3 (2.25 g, 5.0 mmol), and carbon tetrabromide (2.49 g, 7.5 mmol) in dichloromethane (15 ml). After the addition, the mixture was stirred at room temperature overnight and then washed with water (60 ml), brine, dried (MgSO$_4$) and the solvent was removed in vacuo. Purification by silica gel column chromatography using hexane-ethyl acetate (3:1) as the eluant gave 8 (1.29 g, 50%) as an oil.

$^1$H NMR (CDCl$_3$, 2 Hz) 200 MHz) δ1.75–2.05 (2H, m); 3.40 (2H, m); 3.63–3.90 (2H, m); 4.65 (1H, m); 5.15 (2H, s); 5.90 (1H, br.s); 6.90 (1H, s); 7.32 (15H, m).

REFERENCE EXAMPLE 9

Diphenylmethyl 2-N-benzyloxycarbonylamino-5-bromo-4-(azetidin-2-one-4-yl)oxypentanoate (3)

Method A:

Lithium bromide was added to a solution of tosylate 7 (1.9 9, 2.82 mmol) in hexamethylphospholic triamide (HMPA) (20 ml) and the mixture was heated at 60° C. under nitrogen atmosphere for 3 h. The solution was poured into cold water (250 ml) and extracted with ethyl acetate (3×150 ml). The ethyl acetate portion was washed with water (3×100 ml), brine, dried (MgSO$_4$) and the solvent was removed in vacuo. Purification by silica gel column chromatography using hexane-ethyl acetate as the eluant gave 9 (1.02 9, 62%) as a white foam.

$^1$H NMR (CDCl$_3$, 200 MHz) (Mixture of diastereomers) δ: 1.75–1.99 (2H, m); 2.56–2.63 (1H, m); 2.80–2.98 (1H, m); 3.53–3.66 (3H, m); 4.21 (1H, m); 4.91–5.07 (3H, m); 6.72 (1H, s); 7.28 (15H, s); 7.83 (1H, br.s); 8.45 (1H, br.s).

IR (Neat): 3340, 3005, 1766, 1745 cm$^{-1}$.

Method B:

Triethylamine (0.52 ml, 3.71 mmol) and palladium (II) acetate (0.083 g, 0.37 mmol) was added to a stirred solution of 4-acetoxy azetidinone (0.48 g, 3.71 mmol) and bromohydrin 8 (0.95 g, 1.85 mmol) in benzene (50 ml). The mixture was stirred for 20 h at room temperature under nitrogen atmosphere and filtered through a pad of celite. The celite was washed with ethyl acetate (100 ml) and the combined organic layer was washed with water (40 ml), brine, dried (MgSO$_4$) and the solvent was removed in vacuo. Purification by silica gel column chromatography using hexane-ethyl acetate (1:1) as the eluant gave 9 (0.22 g, 30%) as a foam.

REFERENCE EXAMPLE 10

N-Benzyloxycarbonyl-3-[(3RS,5SR)-7-oxo-1-aza-4-oxabicyclo [3.2.0]hept-3-yl]-L-alanine diphenylmethyl ester(10A) and N-(benzyloxycarbonyl)-3-[(3RS,5SR)-7-oxo-1-aza-4-oxa bicyclo[3.2.0]hept-3-yl]-D-alanine diphenylmethyl ester(10B)

Method A:

Silver 6,6,7,7,8,8-heptafluoro-2,2-dimethyl-3,5-octanedionate (FOD) (0.75 g, 1.86 mmol) was added to a solution of the bromide 9 (0.47 g, 0.81 mmol) in dimethylformamide (DMF) (20 ml) and the reaction mixture was heated at 60° C. under nitrogen atmosphere for 20 h. Ethyl acetate (200 ml) was added and the mixture was filtered through a pad of celite. The ethyl acetate solution was washed with brine (3×100 ml), dried (MgSO$_4$) and the solvent was removed in vacuo. Purification by silica gel column chromatography using hexane-ethyl acetate (1:1) as the eluant gave 10 (0.18 g, 45%) (mixture of isomers—see Method B) as a pale yellow foam.

Method B:

Cesium carbonate (0.32 g, 0.98 mmol) was added to a semi-cold (4° C.) solution of the bromide 8 (0.57 g, 0.98 mmol) in dimethylsulfoxide (DMSO) (10 ml). The mixture was stirred for 30 min under nitrogen atmosphere and then poured into water (200 ml). The resulting mixture was extracted with ethyl acetate (3×100 ml) and the ethyl acetate portion was washed with brine, dried (MgSO$_4$) and the solvent was removed in vacuo. Purification by silica gel column chromatography using hexane-ethyl acetate (2:1) as the eluant gave a major and minor isomer wick a total yield of 0.24 g (49%). The proton nmr data of the major isomer was identical to that reported for diprotected clavalanine (J. Org. Chem. 12, 3457 (1985)).

10A (Major Isomer)

$^1$H NMR (CDCl$_3$, 200 MHz) δ: 2.02 (2H, dd, J=5.1, 6.0 Hz); 2.47 (1H, dd, J=7.0, 11.5 Hz); 2.67 (1H, d, J=16.5 Hz); 3.20 (1H, dd, J=2.8, 16.5 Hz); 3.79 (1H, dd, J=6.1, 11.6 Hz); 3.99 (1H, d, J=6.3 Hz); 4.71 (1H, m); 5.11 (2H, s); 5.24 (1H, d, J=2.5 Hz); 5.75 (1H, d, J=8.9 Hz); 6.91 (1H, s); 7.53 (15H, br.m).

IR (Heat): 3420, 3056, 1782, 1765, 1567, 1506 cm$^{-1}$.

10B (Minor Isomer):

$^1$H NMR (CDCl$_3$, 200 MHz) 8: 2.06 (2H, dd, J=5.7, 6.2 Hz); 2.46 (1H, dd, J=6.4, 11.5 Hz); 2.53 (1H, d, J=16.3 Hz); 2.96 (1H, dd, J=2.5, 16.2 Hz); 3.84 (1H, dd, J=5.4, 11.5 Hz); 4.27 (1H, m); 4.55 (1H, m); 4.66 (1H, d, J=2.5 Hz); 5.03 (2H, s); 5.55 (1H, d, J=8.5 Hz); 6.87 (1H, s); 7.25 (15H, br, m).

IR (Neat): 3360, 3065, 2960, 1781, 1745, 1718, 1561 cm$^{-1}$.

REFERENCE EXAMPLE 11

3-[(3RS,5SR)-7-oxo-1-aza-4-oxabicyclo[3,2,0]hept-3-yl]-L-alanine (11)

Palladium on activated carbon (10%, 53.8% moist.) was added to a solution of disubstituted alanyl clavam 10A . (0.07 g, 0.14 mmol) in methanol (25 ml)—ethyl acetate (10 ml). The mixture was hydrogenolysed at 50 psi for 1.5 h and filtered through a pad of celite. The celite was washed with methanol (30 ml) and the combined methanol solution was removed in vacuo. Water (10 ml) was added and the solution was washed with ethyl acetate (20 ml). The aqueous layer was freeze-dried to give 11 (18 mg, 67%) as an off-white solid.

$^1$H NMR (D$_2$O, 200 MHz) δ: 2.21 (2H, m); 2.78 (dd, 1H, J=7.4, 11.7 Hz); 2.97 (1H, d, J=17.0 Hz); 3.41 (1H, dd, J=2.9, 16.8 Hz); 3.96 (1H, t, J=5.2 Hz); 4.08 (1H, dd, J=6.2, 11.9 Hz); 4.43 (1H, m); 5.48 (1H, d, J=2.7 Hz).

IR (Nujol): 3170, 1775, 1774, 1712, 1660 cm$^{-1}$.

REFERENCE EXAMPLE 12

3-[(3RS,5SR)-7-oxo-1-aza-4-oxabicyclo[3.2.0]hept-3-yl]-D-alanine (12)

By following the procedure as described in Example 11, the title compound was obtained in 92% yield from the deprotection of compound 10B.

$^1$H NMR (D$_2$O, 200 MHz) δ: 2.21 (2H, m) ; 2.78 (dd, 1H, J=6.9, 11.3 Hz); 2.96 (1H, d, J=17.1 Hz); 3.41 (1H, dd, J=2.3, 16.5 Hz); 3.86 (1H, m); 4.10 (1H, dd, J=6.2, 11.8 Hz); 4.59 (1H, m); 5.46 (1H, d, J=2.7 Hz).

IR (Nujol): 3370,3280,1772,1534 cm$^{-1}$.

TEST EXAMPLE 1

In vitro KB Cell Cytotoxicity Assay

In vitro KB cell cytoxocity assay was done by modification of the crystal violet assay (Grillis et al., Anal Biochem., 159, 109–113 (1986).

KB cells were cultivated in Eagles minimum essential medium supplemented with 10% calf serum and incubated at 37° C. in a humidified 5% CO$_2$ atmosphere to prepare a cell stock. Cells were counted using a neubauer hemocytometer and seeded in 96 well plates at 100 μl of 3×10$^4$ cells/ml and cultured for one day. Test compounds were diluted and 100 μl of the solution was added in triplicate wells to give final concentration of 10, 5, 1, 0.5, 0.1, 0.05 and 0.01 μg/ml. Control wells were identical except that test compound was absent. These were cultured for three days. Then the cells were fixed with addition of 20 μl of 25% glutaraldehyde for 15 minutes, washed with water and dried. Then stained with 100 μl of 0.05% crystal violet for 15minutes, washed with water and dried. The wells are eluted with 100 μl of 0.05M NaH$_2$PO$_4$/ethanol (1:1 v/v) and read at OD$_{540}$ on a multiscan spectrophotometer. Inhibition value of cell Growth was calculated based on optical density using the following equation;

$$\% \text{ inhibition} = \frac{\text{untreated} - \text{treated}}{\text{untreated}} \times 100$$

TD$_{50}$ values were calculated from linear recression ines of the log-logit plot.

The compound of formula (I) was assayed by this method against KB cell lines and their TD$_{50}$ values are reported in Table 1.

TEST EXAMPLE 2

Vitro L1210 Cell Cytoxocity Assay

In vitro :L1210 cell cytotoxicity assay was done by the method of microculture tetrazolium assay (Alley et al., Cancer Research, 48, 589–601 (1988).

L1210 cells were cultivated in RPMI 1640 medium supplemented with 10% fetal calf serum and 50 μl of 2-mercaptoethanol at 37° C. in humidified 5% CO$_2$ atmosphere no prepare a cell stock. Cells were counted using neubauer hemocytometer and seed in 96 well plates at 100 μl of 0.5×10$^4$ cells per ml. The test compounds were diluted and 100 μl of the solution was added in triplicate wells to give the final concentration of 10, 5, 1, 0.5, 0.1, 0.05 and 0.01 μg/ml. Control wells were identical except :hat the test compound was absent. These were cultured for three days. Results were assayed using the microculture tetrazolium assay briefly. 50 μl of MTT formazoan working solution (1:5 v/v in culture medium) was added to each well and cultures were incubated at 37° C. for 4 hrs. Culture plates were centrifuged at low speed for 5 minutes. All but 10–20 μl of culture medium supernatant was removed by slow aspiration and replaced by mechanical shaker and read at OD$_{540}$ on a multiscan spectrophotometer. Inhibition value of cell growth was calculated based on optical density using the following equation;

$$\% \text{ inhibition} = \frac{\text{untreated} - \text{treated}}{\text{untreated}} \times 100$$

TD$_{50}$ values were calculated from linear depression ines of the log-logit plot.

The compound of formula (I) was assayed by this method against L1210 cell lines and their TD$_{50}$ values are reported in Table 2.

TABLE 1

In Vitro Cell Toxicity of Compound of General Formula (I)

| Reference Example No. | stereo in alanine moiety | R | R$_1$ | Cytotoxicity TD$_{50}$ (μg/ml) KB | L-1210 |
|---|---|---|---|---|---|
| 10A | L | COOCH$_2$C$_6$H$_5$ | CH(C$_6$H$_5$)$_2$ | 3.17 | 10.0 |
| 10B | D | COOCH$_2$C$_6$H$_5$ | CH(C$_6$H$_5$)$_2$ | 1.78 | 7.50 |
| 11 | L | H | H | 0.023 | 0.10 |
| 12 | D | H | H | 0.098 | — |

TEST EXAMPLE 3

In Vivo Antitumor Activity Against Sarcoma 180

The compounds of general formula (I) were tested in vivo against Sarcoma 180 xenografted tumor to mice as illustrated herein after.

Sarcoma 180, 5×10$^6$ cells were inoculated by S.C. to male ICR mice (6 weeks old) on day 0. Drugs were administered on days 1,5 and 9. Mice were killed and tumor weight was measured on day 12 after transplantation. The percentage inhibition of tumor growth was calculated from the mean tumor weight of the treated group compared with that of the control group. Number of mice used in each group was between 6 to 10. The percentage inhibition of tumor Sarcoma 180 group by compound of formula (I) are summarized in Table 2.

TABLE 2

Effect of Compounds of Formula (I) against Sarcoma 180 (s.c. - i.p.) in Male ICR

| Reference Example No. | Dose mg/kg/day | Mortality | % Inhibition in 12 days |
|---|---|---|---|
| 11 | 3.13 | 0/7 | 79.5 |
|  | 1.56 | 0/7 | 71.4 |

We claim:

1. A composition comprising an effective amount of the 3-(7-oxo-1-aza-4-oxabicyclo[3.2.0]hept-3-yl)alanine derivative according to formula (I)

[Chemical structure of formula (I)]

or a pharmaceutically acceptable salt thereof wherein

R is hydrogen or COOR$_2$ wherein R$_2$ is a C$_1$–C$_3$ alkyl group which is unsubstituted or substituted with a 1–3 aryl group; and R$_1$ is hydrogen or a C$_1$–C$_3$ alkyl group which is unsubstituted or substituted with a 1–3 aryl group; in combination with a pharmaceutically acceptable carrier.

2. The composition according to claim 1, wherein R is $COOR_2$ and $R_2$ is selected from the group consisting of hydrogen, methoxycarbonyl, ethoxycarbonyl and benzyloxycarbonyl.

3. The composition according to claim 2, wherein R is $COOR_2$ and $R_2$ is selected from the group consisting of hydrogen and benzyloxycarbonyl.

4. The composition according to claim 1, wherein $R_1$ is selected from the group consisting of hydrogen, methyl, benzyl and diphenylmethyl.

5. The composition according to claim 4, wherein $R_1$ is selected from the group consisting of hydrogen and diphenylmethyl.

6. The composition according to claim 1, wherein the derivative of formula I includes a bicyclic nucleus which carries two asymmetric carbon atoms at positions 3 and 5, wherein said derivative exists as one or more of four possible disastereoisomers.

7. The composition according to claim 6, wherein said derivative exists as a (3R,5S) or a (3S,5R) isomer or a mixture thereof.

8. The composition according to claim 1, wherein an alanine chain at $C_3$ of the bicyclic nucleus carries one asymmetric carbon atom and said derivative exists as both a D and an L isomer.

9. A method for treating solid tumors or leukemia sensitive to compounds below in a mammal in need of such treatment, comprising administering to said mammal an effective amount of the derivative according to formula (I):

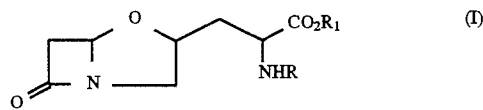

10. The method according to claim 9, wherein said solid tumors are selected from the group consisting of gastrointestinal tract, lung, breast, liver and uterine tumors.

11. The method according to claim 9, wherein said effective amount of the derivative according to formula (I) is between 50–1000 mg per day.

* * * * *